United States Patent
Glynn et al.

[11] Patent Number: 5,415,634
[45] Date of Patent: May 16, 1995

[54] CATHETER HAVING HELICAL INFLATION LUMEN

[75] Inventors: Brian Glynn, Sunnyvale; John B. Simpson, Woodside; Michael Evans, Palo Alto, all of Calif.

[73] Assignee: Devices For Vascular Intervention, Inc., Redwood City, Calif.

[21] Appl. No.: 874,346

[22] Filed: Apr. 24, 1992

Related U.S. Application Data

[63] Continuation-in-part of Ser. No. 572,521, Aug. 23, 1990, abandoned.

[51] Int. Cl.⁶ .......................................... A61M 29/00
[52] U.S. Cl. ...................................... 604/96; 604/103; 604/280; 604/282; 606/192; 606/194
[58] Field of Search .................. 604/96, 103, 280, 282; 606/192, 194, 159

[56] References Cited

U.S. PATENT DOCUMENTS

| | | | |
|---|---|---|---|
| 4,425,919 | 1/1984 | Alston, Jr. et al. | 604/282 |
| 4,545,390 | 10/1985 | Leary . | |
| 4,669,469 | 6/1987 | Gifford, III et al. | 606/159 |
| 4,762,130 | 8/1988 | Fogarty et al. | 604/96 |
| 4,817,613 | 4/1989 | Jaraczewski et al. | 604/282 |
| 4,889,137 | 12/1989 | Kolobow . | |
| 4,900,314 | 2/1990 | Quackenbush | 604/282 |
| 5,015,230 | 5/1991 | Martin et al. . | |
| 5,071,425 | 12/1991 | Gifford, III et al. | 606/159 |

FOREIGN PATENT DOCUMENTS 0163502 12/1985 European Pat. Off. .

*Primary Examiner*—C. Fred Rosenbaum
*Assistant Examiner*—N. Kent Gring
*Attorney, Agent, or Firm*—Townsend and Townsend Khourie and Crew

[57] ABSTRACT

A vascular catheter includes a catheter body, an inflatable balloon disposed at the distal end of the catheter body, and an inflation conduit extending from the proximal end of the catheter body to the inflatable balloon. The inflation conduit is disposed on the exterior of the catheter body, minimizing the total cross-sectional area but imparting a non-circular periphery. Catheter whip resulting from the non-circular periphery is reduced by arranging the inflation conduit in a helical pattern over at least a distal portion of the catheter body.

27 Claims, 3 Drawing Sheets

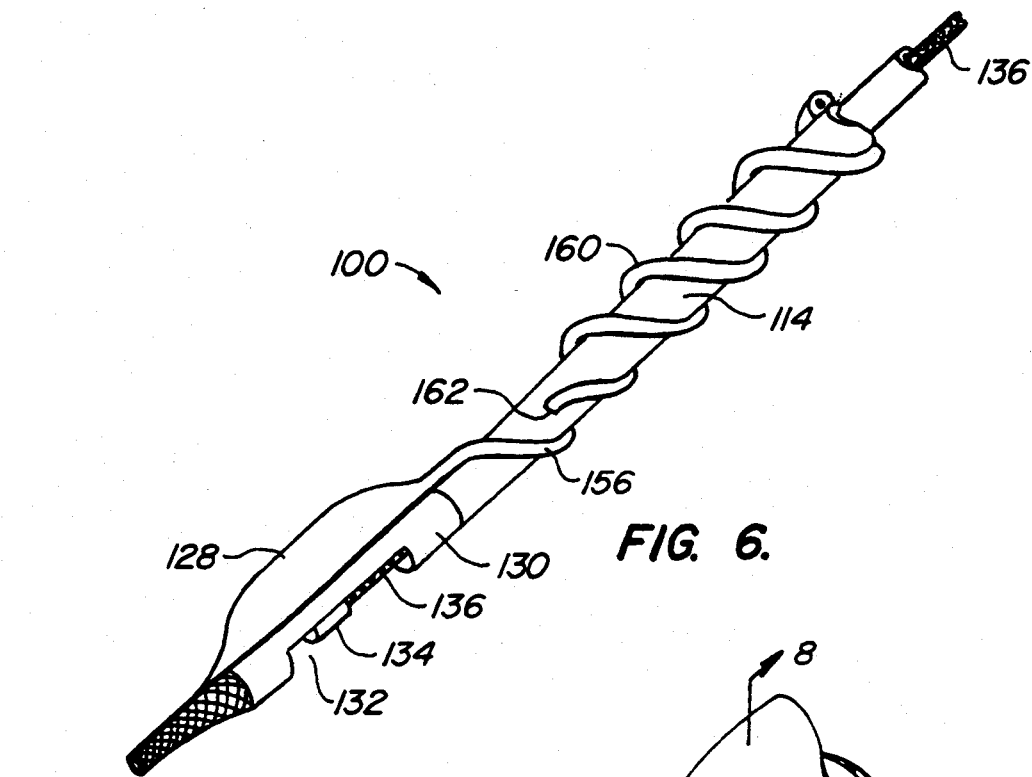
FIG. 6.
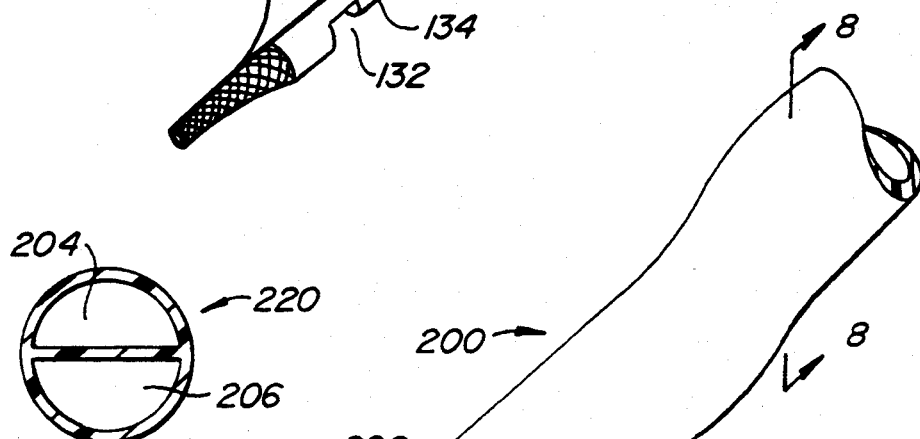
FIG. 7.
FIG. 9.
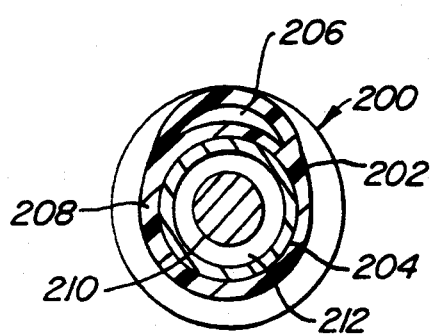
FIG. 8.

CATHETER HAVING HELICAL INFLATION LUMEN

CROSS-REFERENCE TO RELATED APPLICATIONS

This application is a continuation-in-part of application Ser. No. 07/572,521, filed Aug. 23, 1990, now abandoned, and is related to Applicants' application Ser. No. 07/449,014, filed on Dec. 1, 1989, the disclosures of which are incorporated herein by reference. The latter application is a continuation-in-part of Ser. No. 07/243,397, now abandoned.

BACKGROUND OF THE INVENTION

1. Field of the Invention

The present invention relates generally to the construction of vascular catheters. In particular, the present invention relates to catheters that require an inflation lumen connecting a proximal source of inflation medium with an inflatable element, such as a balloon, at the distal end of the catheter.

Atherosclerosis is a condition characterized by fatty-like deposits (atheromas) in the intimal lining of a patient's arteries. Atherosclerosis can have many symptomatic manifestations, including angina, hypertension, myocardial infarction, strokes, and the like. Initially, the atheromas deposited in the blood vessels are relatively soft and tractable; however, over time they become calcified and hardened.

Numerous approaches for reducing and removing such vascular deposits have been proposed, including balloon angioplasty, where a balloon-tipped catheter is used to dilatate a region of atheroma; atherectomy, where a blade or other cutting element is used to sever and remove the atheroma; and laser angioplasty, where laser energy is used to ablate at least a portion of the atheroma. In addition to such therapeutic approaches, a variety of techniques for transluminal imaging of atheroma and other diseased regions of a blood vessel has been proposed, including endoscopic imaging and ultrasonic imaging techniques.

Many of such techniques require the use of an inflatable element, such as a balloon, located near the distal end of the catheter. Balloon angioplasty, of course, utilizes a distal balloon as the primary interventional element. In addition, atherectomy, laser angioplasty and transluminal imaging may all utilize a balloon to position the distal end of the catheter within a blood vessel.

Of particular interest are atherectomy procedures which utilize special catheters having a severing instrument located at a distal end thereof and an inflatable balloon located opposite the severing instrument. The catheter is positioned within the vascular system so that the severing instrument lies adjacent the atheroma, and the balloon is inflated to bring the severing instrument into close proximity with the atheroma. The severing instrument is then actuated to excise the atheroma, and the severed material captured to prevent the release of emboli. The severing instrument on the atherectomy catheter can take a variety of forms, including fixed blades (requiring movement of the entire catheter to effect cutting) and movable blades which can be actuated without movement of the catheter as a whole. The present invention, however, is not limited to atherectomy catheters and instead is broadly adaptable to catheters that employ inflation techniques with a wide variety of interventional and imaging implements mounted in a distal housing.

Intravascular catheters are usually designed to be symmetric about their longitudinal axis. Preferably, the catheters have a circular cross-section in order to facilitate translation and rotation of the catheter within the patient's vascular system. Whenever an inflation balloon is placed at the distal end of the catheter, it is desirable that an inflation lumen be integrated into the catheter body without destroying the catheter's symmetric shape. This may be done in a variety of ways. For example, lumens may be formed in the wall of the catheter body while maintaining a desired symmetry. Alternatively, separate inflation tubes may be disposed within larger lumens within the catheter and connected with the distal balloon. A third approach is to form a coaxial sheath about the catheter body, where the sheath provides an annular lumen which may be connected to the balloon. Although each of these approaches maintains the desired symmetry, they each require that the overall cross-sectional area of the catheter be increased. Such an increase in area is undesirable, particularly when the catheter is to be used in coronary procedures or when it must pass through tight lesions.

Thus, in some cases, it would be desirable to reduce the total cross-sectional area of intravascular catheters to facilitate passage of the catheter through tight, tortuous regions of the vascular system even if such reduction requires a non-symmetric design. One way this may be accomplished is to provide an inflation lumen or tube external to the catheter body. Such a design eliminates unnecessary material in the catheter body which would be necessary in order to provide symmetry.

Whenever an external inflation lumen is provided on an otherwise symmetric catheter body, the resulting ridge gives the catheter a non-symmetric shape. The non-symmetric shape may be acceptable for those applications in which rotational movement of the catheter is not required (e.g. balloon angioplasty with symmetric balloons) or is not constrained by the vessel walls; however, under tight-fitting conditions, use of such a non-symmetric catheter can be problematic. In particular, the non-symmetric shape can give rise to a phenomenon known as "catheter whip." Catheter whip occurs whenever the operator of the catheter attempts to rotate the catheter within the vascular lumen to rotationally align with a predetermined site of occlusion. When the operator must rotate the catheter, and the vessel passage is too narrow, the ridge presented by the external lumen of conventional designs can resist the motion. This resistance causes the buildup of potential energy (i.e., through a rotational wind-up) that can be released suddenly upon application of additional rotational force. This sudden release of energy resulting in uncontrolled rotational motion is known as "catheter whip." Catheter whip can similarly be induced upon application of torque to catheters having fixed cutting members at their distal ends to remove deposits from the vessel wall by rotation of the entire catheter. See, e.g., U.S. Pat. Nos. 4,627,436 and 4,685,458.

For the above reasons, it is desirable to provide intravascular catheters that have a symmetric or nearly symmetric shape without incorporating excess structural material which restricts the catheter's ability to enter narrow passageways. Such a design is expected to greatly reduce the occurrence of catheter whip.

2. Description of the Background Art

Atherectomy catheters having symmetric cross-sections with internal inflation lumens are described in European patent application 163 502 and U.S. Pat. No. 4,669,469. An embolectomy catheter having an external helical balloon at its distal end is described in U.S. Pat. No. 4,762,130. An atherectomy catheter having a non-symmetric construction is described in U.S. Pat. No. 5,071,425, the disclosure of which is incorporated herein by reference.

SUMMARY OF THE INVENTION

According to the present invention, a vascular catheter comprises a flexible tube having proximal and distal ends and a substantially circular cross-sectional profile. An external inflation conduit extends from the proximal to distal end of the flexible tube and is arranged helically over at least a distal portion of the exterior, optionally being arranged helically over the entire length hereof. An inflatable balloon is located at the distal end of the flexible tube, and the external inflation conduit provides an inflation lumen for the balloon. The inflation conduit may be formed integrally with the flexible tube or may be a separate tube affixed to the exterior of the flexible tube. The helical configuration of the inflation conduit at least partly overcomes the problems associated with catheter whip, as described above, while minimizing the combined cross-sectional areas of the flexible tube and inflation conduit.

In a preferred embodiment, the catheter is an atherectomy device which includes a cutting member at its distal end and can be used to remove atheromas from blood vessels. The present invention, however, is not limited to atherectomy catheters and can be adapted to the construction of laser ablation catheters, imaging catheters, asymmetric dilatation catheters and virtually any catheter which utilizes an inflatable balloon at its distal end and which requires rotation of the catheter for positioning or use within the vascular system.

In a further preferred aspect of the present invention, the eccentricity of the combined flexible tube and inflation conduit is minimized while still allowing a sufficiently sized inflation lumen to permit adequate deflation of the balloon. Slow balloon deflation times can be problematic, but it has been found that a crescent-shaped lumen can provide a low conduit profile while providing an adequate cross-sectional lumen area.

In a particularly preferred embodiment, the inflation conduit is formed integrally with the flexible tube and has a crescent-shaped cross-sectional profile which minimizes the cross-sectional area of the catheter presented within the vascular system. It has been found that this design is particularly effective in reducing the incidence of catheter whip during use.

BRIEF DESCRIPTION OF THE DRAWINGS

FIG. 6 is a perspective view of the distal end of a catheter similar to that of FIG. 1, further including a second helical inflation lumen which is open at its distal end to act as an aspiration or perfusion lumen.

FIG. 7 is a detail view of another alternate construction of the catheter of the present invention, where the inflation lumen has a reduced profile and crescent-shaped cross-section.

FIG. 8 is a cross-sectional view taken along line 8—8 of FIG. 7.

FIG. 9 is a cross-sectional view of a preferred tubing which can be used in fabrication of catheter bodies of the type illustrated in FIGS. 7 and 8.

DESCRIPTION OF THE SPECIFIC EMBODIMENTS

Vascular catheters according to the present invention will include an elongate catheter body having proximal and distal ends. The catheter bodies will be very flexible to facilitate passage of the catheter within a patient's vascular system, but will have sufficient torsional stiffness to allow the distal end of the catheter to be rotationally positioned by rotational torque applied to the proximal end of the catheter body. The catheters will include inflatable balloons at their distal ends and will further include inflation conduits extending from the proximal end of the catheter body to the inflatable balloon to allow remote balloon inflation while the catheter is positioned within the vascular system. The catheter body will typically have a length from about 60 to 150 cm and a diameter from about 3 to 11 French (F; 0.33 mm). For use in coronary applications, the catheter body will typically have a length from about 120 to 150 cm, and a diameter from about 3 to 6 French (F), while for peripheral applications, the catheter body will have a length from about 60 to 110 cm and a diameter from about 3 to 11 F.

According to the present invention, the inflation conduit will be disposed helically on the outside of the catheter body, either as a separate tube or as an integral portion of the catheter body. The inflation conduit will be substantially non-expandable, even when internally pressurized by an inflation or other medium. In this way, the total cross-sectional area of the catheter body may be reduced while the helical arrangement of the inflation conduit ameliorates the problems associated with a non-symmetric catheter profile.

General considerations relating to the design and construction of atherectomy catheters are described in copending applications Ser. No. 07/298,846 and Ser. No. 07/405,906, the disclosures of which are incorporated herein by reference. The constructions of the present invention may also find use with balloon-assisted vascular incision devices as described in copending application Ser. Nos. 07/142,382 and 07/243,397, the disclosures of which are incorporated herein by reference.

Figure 1:
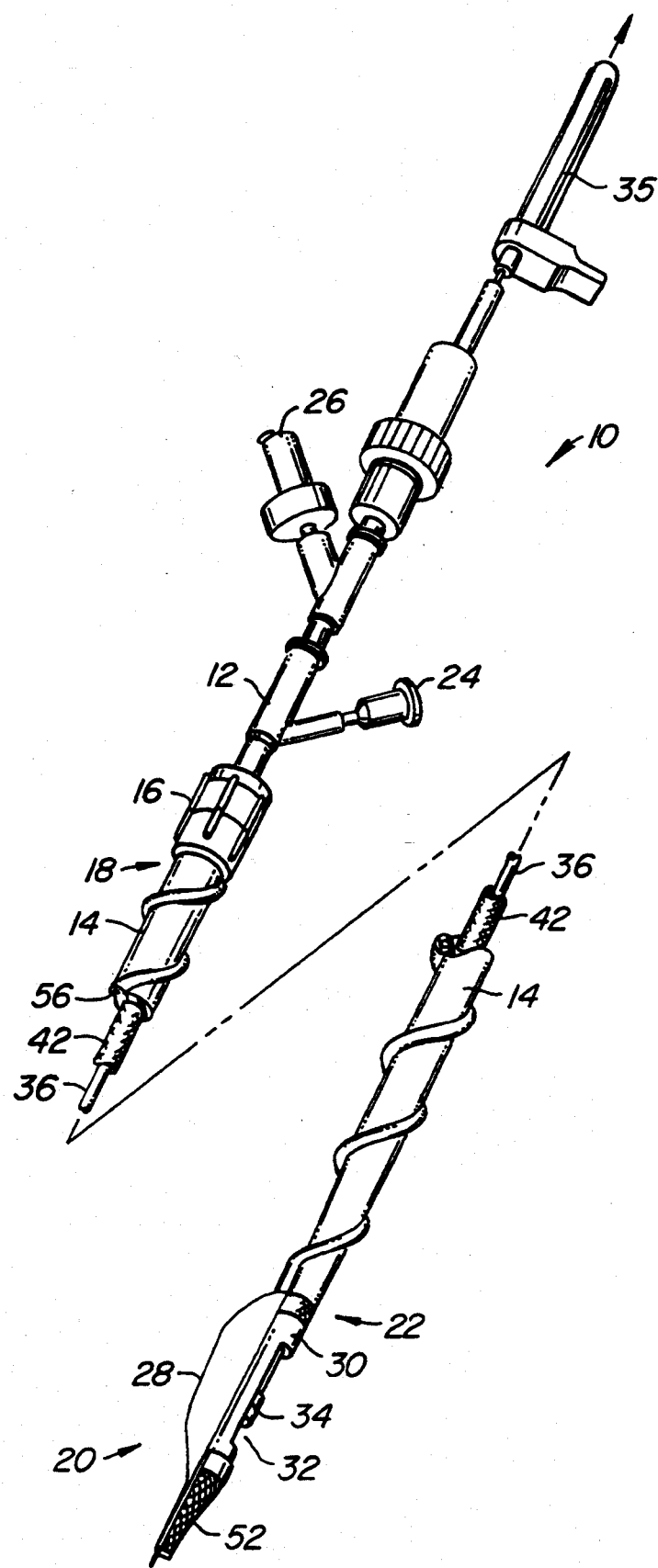
FIG. 1 is a perspective view of a catheter constructed in accordance with the principles of the present invention.
Figure 2:
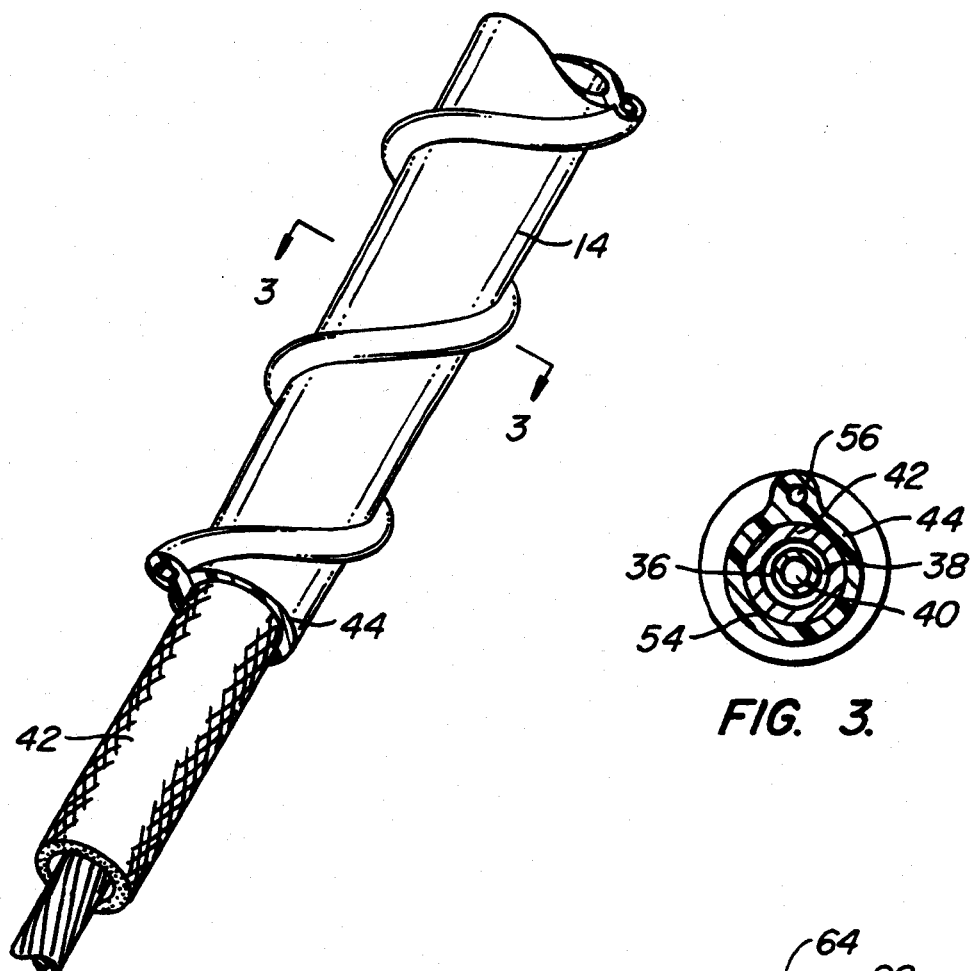
FIG. 2 is a detail view of the catheter of FIG. 1, with portions broken away.
Figure 3:
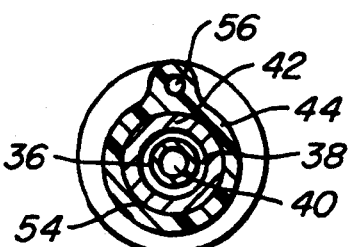
FIG. 3 is a cross-sectional view taken along line 3—3 of FIG. 2.

Referring to FIGS. 1-3, a vascular catheter 10 includes a housing 12 attached to a flexible catheter body 14 via a proximal housing 16. The proximal housing 16 includes a conventional rotatable fitting for joining the housing to the catheter body. The proximal housing 16 is located at a proximal end 18 of the catheter body 14, and an interventional and/or imaging device 20 is located at distal end 22 of the catheter body 14. A balloon port 24 and flush port 26 are connected to housing 12, as described in greater detail hereinafter. The balloon port 24 provides an inlet for a relatively incompressible fluid, e.g., saline or contrast medium, which is used to inflate an inflatable balloon 28 which forms part of the interventional and/or imaging device 20, as described in greater detail hereinafter.

When the catheter 10 is an atherectomy catheter, a distal housing 30 having an elongate aperture 32 is attached to the distal end 22 of catheter body 14. A circular (cup-shaped) cutting blade 34 is attached to the distal end of a torque cable 36 which extends through a central lumen 38 (FIG. 3) of the catheter body 14. The torque cable 36 preferably includes a guide wire lumen 40 which may be used in positioning the catheter 10 over a movable guide wire in a conventional manner. A driver connection 35 is attached to the proximal end of torque cable 36, and is able to rotate and axially translate the cable, typically using a motor drive unit (not illustrated) such as that described in U.S. Pat. No. 4,771,774, the disclosure of which is incorporated herein by reference. The design and construction of housing 12 is conventional and need not be described further.

The catheter body 14 is that portion of the atherectomy catheter 10 which extends from the proximal housing 16 to the cutter housing 30. The catheter body 14 must have a sufficient flexural resilience and torsional stiffness to allow the catheter to be positioned and manipulated within a patient's vascular system. In particular, it is necessary that the physician employing the catheter 10 be able to rotationally position the distal housing 30 so that aperture 32 is located adjacent the stenotic material which is to be severed. To achieve the proper balance of flexural resilience and torsional stiffness, the catheter body 14 may be formed as a laminate structure including an inner torque member 42 and an outer tube member 44, where the torque member is fixedly attached to the catheter body 14 so that rotation of proximal housing 16 will result in a corresponding rotation of the cutter housing 30.

The torque member 42 will normally be a braided metal cable, typically a stainless steel braided cable, as described in co-pending application Ser. No. 07/298,846, the disclosure of which has previously been incorporated herein by reference. It is important that the torque member be highly flexible, yet remain capable of transmitting torque along its entire length with a minimal loss of transmission efficiency. The diameter of the torque member 42 will vary depending on the intended application of catheter 10, generally being in the range from about 1 mm to 4 mm, usually being in the range from about 2 to 4 mm for peripheral arteries and in the range from about 1 to 2 mm for coronary arteries.

The torque cable 36 extends through the lumen 38 of torque member 42, and has a diameter in the range from about 0.4 mm to 1.5 mm, usually being in the range from about 0.5 mm to 1.0 mm. Conveniently, the torque cable 36 may be formed from multi-stranded stainless steel wire. If it is desired to pass a steerable guide wire through the center, the cable 36 should be formed into a tube, typically a braided tube, such as a stainless steel braid, coated with a plastic, such as a urethane, and having the guide wire lumen 40 extending axially therethrough.

Distal housing 30 is generally a hollow cylindrical structure which is fixedly attached to the distal end of torque member 42, thus forming an extension thereof. The cutter housing 30 will usually be a rigid structure, typically formed from stainless steel or other surgically acceptable metals, but may also be a flexible structure as described in U.S. Pat. No. 4,781,186, the disclosure of which is incorporated herein by reference. Elongate aperture 32 is formed on one side of the cutter housing 30, and cup-shaped cutting blade 34 is rotatably mounted within the interior thereof. The length of the cutter housing 30 is not critical, typically being in the range from about 10 mm to 50 mm, usually being in the range from 12 mm to 40 mm. The elongate aperture 32 will typically have a length in the range from about 5 mm to 45 mm and a width in the range from about 1 mm to 4 mm. The cutting blade 34 is attached to the distal end of torque cable 36, so that the blade 34 may be rotated and axially translated by manipulation of the driver member 44. Conveniently, motorized means for rotating and translating the cutter blade may be provided, as described in co-pending U.S. Pat. No. 4,771,774, previously incorporated herein by reference.

Inflatable balloon 28 is located on cutter housing 30 on the side opposite to aperture 32. The inflatable balloon 28 will be transparent and usually, though not always, formed integrally as an expanded region of an inflation conduit 56, as described in more detail hereinafter. Typically, the balloon will have a width, when fully inflated, of approximately 1 mm to 6 mm, more usually about 2 mm to 4 mm.

A flexible open-ended tip 52 is attached to the distal end of cutter housing 30, forming a continuous interior volume therewith. The interior volume of the tip 52 is capable of receiving and retaining atheroma material which is severed by blade 34 as it is brought forward in the housing 30. The flexible tip 52 also facilitates positioning the catheter 10 over a conventional guidewire (not illustrated) in the vascular system. The flexible tip 52 is conveniently formed from a braided material typically braided stainless steel, and is attached to the cutter housing 30 by conventional means.

In the specific embodiment illustrated in FIGS. 1-3, the tube member 44 of catheter body 14 is a multiple lumen flexible tube including at least a first lumen 54 and a second lumen 56. The torque member 42 is disposed in the first lumen 54, while the second lumen 56 provides the inflation conduit which connects the inflatable balloon 28 to balloon port 24. The tube member 44 usually, though not always, will be composed of a translucent or transparent thermoplastic material, such as a heat-shrinkable polyolefin. Preferably, tube member 44 will be made of a surlyn or polyethylene material. Conveniently, the catheter body 14 may be formed by heating the multiple lumen flexible tube and expanding the first lumen 54 so that the torque member 42 may be inserted. The tube may then be twisted so that the desired helical pattern is imparted to lumen 56. The first lumen 54 may then be constricted about the torque member 42 in a conventional manner.

A principal distinction of the present invention over previous catheter designs involves provision of inflation lumen 56 as a helically disposed passageway about first lumen 54. The helical displacement of lumen 56 greatly reduces the non-symmetrical structure for the catheter body 14 that occurs when the inflation lumen is provided as a straight tube along the central axis and exterior to the catheter body. As a more nearly symmetrical structure is produced by the helical disposition of inflation lumen 56, incidences of "catheter whip" are minimized.

Figure 5:
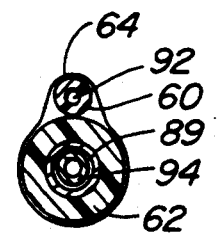
FIG. 5 is a cross-sectional view taken along line 5—5 of FIG. 4.
Figure 4:
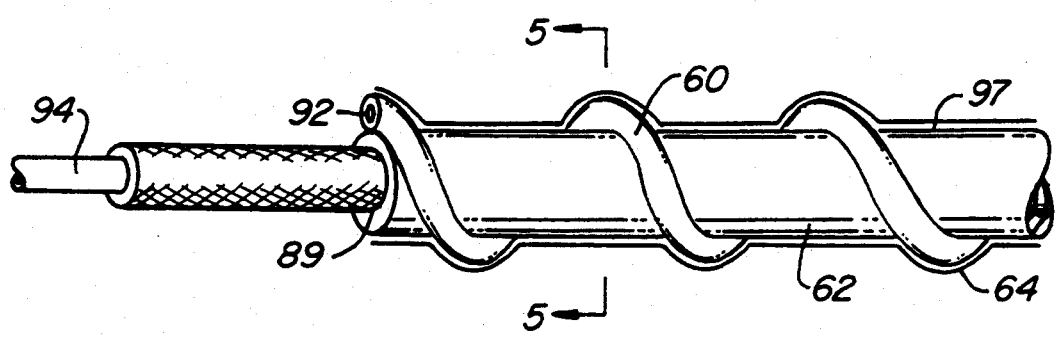
FIG. 4 is a detail view of an alternate construction of the catheter body of the present invention, where the inflation conduit is formed as a separate tube.

The helical inflation conduit that defines the inflation lumen can be provided either integrally within a flexible tube 44 (as illustrated in FIGS. 1-3), or it can be provided as a separate tube 60 wound around a flexible tube 62 having a circular cross-section as illustrated in FIGS. 4 and 5. When the inflation conduit is provided as a separate tube 60, the tube can be affixed to flexible tube 62 via a conventional shrinkwrap plastic sheath 64, or it can be affixed by an adhesive. The preferred mode of attachment is with a shrinkwrap plastic. Suitable shrinkwrap plastics will be composed of cross-linked polyolefins and are well known in the art. When an adhesive is used, flexible tube 62 can be simply dipcoated with the adhesive, then attached to the inflation tube 60. Suitable adhesives are well known to those skilled in the art. The inflation lumen will have an inner diameter of about 0.3–1.0 mm and a thickness of 0.001–0.006 inches. The shrinkwrap will have thickness of about 0.002–0.006 inches. The shrinkwrap or adhesive preferably will be provided over the full length of catheter body 14 but will not extend over the balloon region 28.

In either embodiment, the inflation conduit will usually have a helical pitch of from about 2 to 20 cm/turn, usually being from about 3 to 10 cm/turn. The helical arrangement may extend over the entire length of the flexible tube, or more usually only over a distal portion thereof. In the exemplary embodiment, the inflation conduit will make about 3–10 complete turns over the distal 30 to 50 cm of the catheter body. The proximal portion of the catheter body will usually not enter the narrower portions of the vascular system and is therefore less subject to catheter whip and the other problems described above. The helical turns can be oriented in either a right-handed or left-handed pattern.

The separate inflation tube 60 can be made of any of the softer thermoplastics in order to ensure that it offers little resistance to torsional motion. Preferable materials include surlyn, polyethylene and the like. Desirably, the inflation tube 60 will be made from a transparent plastic to provide good visibility within the inflation lumen.

More than one inflation lumen can be provided in the catheter body. For example, two inflation lumens can be provided which connect to two inflation balloons (not illustrated). Both inflation lumens can be helically wound around the catheter, preferably in a double helix configuration. Also, lumens can be provided with one lumen serving as an inflation lumen and any other lumen(s) serving a different function, such as venting, flushing, etc. When a venting lumen is provided, it can be narrower in diameter than the inflation lumen since the venting lumen serves mainly to permit passage of air exhaust.

The inflation balloon is conveniently formed by expanding the distal end of inflation lumen 56 or inflation tube 60. Expansion is achieved using hot air at an elevated pressure until the desired final dimensions are reached. The proximal portion of inflation lumen 56 can be constrained from expanding during this process by temporarily encasing flexible tube member 44 within a sheath that resists expansion. Usually, the inflation conduit in inflation tube 60 will have a diameter in the range from about 0.015 in. to 0.040 in, while the central lumen will have a diameter in the range from about 0.010 in. to 0.10 in.

Referring now to FIG. 6, a third embodiment of the present invention employing a second helical lumen will be described. The catheter 100 is similar to catheter 10 and includes a proximal housing (not shown) connected to a catheter body 114 by a rotatable fitting (not illustrated). A distal housing 130 is attached to the distal end of the catheter body 114, and a cutting blade 134 is secured to a torque cable 136 allowing the blade to be rotated and translated past an elongate opening 132 in distal housing 130. An inflatable balloon 128 is secured to housing 130 on a side opposite to that of opening 132. Balloon 128 is connected to a first external helical lumen 156 formed on the flexible tube 114. As described thus far, catheter 100 is identical to catheter 10 of FIGS. 1–3.

Catheter 100 further includes a second external lumen 160 formed helically about the exterior of flexible tube 114. As illustrated, the second lumen 160 is formed with a pitch which is identical to that of lumen 156. Such identical pitch allows the two lumens to be space 180° out-of-phase, and the resulting synthetic construction tends to further reduce catheter whip resulting from pressurization of the lumens. As illustrated, the second lumen 160 has an open distal end 162, which allows the lumen to serve as an aspiration or perfusion lumen.

A particularly preferred embodiment of the catheter of the present invention is illustrated in FIGS. 7 and 8. A catheter body 200 comprises a polymeric tube 202 having a first lumen 204 and a second lumen 206. A torque member 208, typically a braided metal cable as described previously, is received in the first lumen 204, and a torque cable 210 extends axially through lumen 212 of the torque member 208.

The second lumen 206 is formed to have a crescent-shaped profile (as described in detail hereinafter) which reduces the total exposed cross-sectional area of the catheter. Typically, the crescent-shaped lumen 206 will subtend at least 45° of the periphery of the catheter body, preferably subtending at least 60° thereof, and frequently subtending 90° or more. By extending the width of the lumen 206 over a greater portion of the peripheral area of the catheter, the height of the lumen can be reduced. Typically, the height of lumen 206 will be no greater than about 0.3 of the diameter of the main body of the lumen, frequently being less than about 0.25 of the main body diameter, and preferably being 0.2 of the diameter or less.

The catheter body 200 having the desired crescent-shaped inflation lumen 206 profile is conveniently fabricated from a thermoplastic tube 220 (FIG. 9) having an "opposed D" profile. The tube 220 will preferably be a thermoplastic, more preferably being a heat shrinkable polyolefin, more preferably being a surlyn. The catheter body 200 is then fabricated by expanding the tube 220 with heat and air pressure and thereafter inserting the torque member 208 therein. The tube is then recovered (using heat without pressure) so that the lumen 204 constricts about the outer surface of the torque member 208. This results in the desired crescent-shaped profile seen in FIGS. 7 and 8. In order to provide for the desired helical disposition, the tube 220 is twisted while the heat is being applied for recovery. Usually, only the distal approximately 20 cm to 50 cm will be twisted and the remainder will be allowed to remain linear. The resulting catheter construction can be utilized in the same manner as the previously discussed embodiments.

The general methodology for fabricating catheters in the manner just described is disclosed in U.S. Pat. No. 5,071,425, the disclosure of which has previously been incorporated herein by reference. That patent, however, discloses neither the helical nature of the inflation lumen of the present invention nor the preferred crescent-shaped profile thereof.

Although the foregoing invention has been described in some detail by way of illustration and example, for purposes of clarity of understanding, it will be obvious that certain changes and modifications may be practiced within the scope of the appended claims. Especially noteworthy in this regard is the fact that the description presented above can readily be extended to make catheters suitable for angioplasty and laser ablation applications.

What is claimed is:

1. A vascular catheter comprising:
   a torsionally reinforced flexible tube having proximal and distal ends and a substantially circular cross-sectional profile;
   an inflatable balloon located at the distal end of the flexible tube; and
   a substantially non-expandable inflation conduit extending from the proximal end to the inflatable balloon, wherein the inflation conduit is arranged helically about at least a distal portion of the exterior of the flexible tube.

2. A vascular catheter as in claim 1, wherein the inflation conduit includes a separate tube wrapped helically about the exterior of the flexible tube.

3. A vascular catheter as in claim 2, wherein the separate helically wrapped tube is secured by a sheath constricted about the flexible tube and the helically wrapped tube.

4. A vascular catheter as in claim 1, wherein the inflation conduit is formed integrally with the flexible tube.

5. A vascular catheter as in claim 4, wherein the inflation conduit has a crescent-shaped profile which subtends at least 45° of the periphery of the flexible tube and extends above the surface of the tube by no more than 0.3 of the tube diameter.

6. A vascular catheter as in claim 1, wherein the inflation conduit has a helical pitch in the range from about 2 to 20 cm/turn.

7. A vascular catheter as in claim 6, wherein the inflation conduit is arranged helically about only a distal portion of the flexible tube, said distal portion having a length from about 30 to 50 cm.

8. A vascular catheter as in claim 6, wherein the inflation conduit is arranged helically over the entire length of the flexible tube.

9. A vascular catheter as in claim 1, further comprising:
   a housing secured to the distal end of the flexible tube; and
   means for severing atheroma disposed on one side of the distal housing;
   wherein the inflatable balloon is disposed on a side of the housing generally opposite to the side on which the severing means is disposed.

10. A vascular catheter comprising:
    a flexible tube having proximal and distal ends, a substantially circular cross-sectional profile, and a central lumen extending axially between the proximal and distal ends;
    a braided metal torque member disposed within the central lumen of the flexible tube and fixed thereto whereby the distal end of the tube can be rotated by applying torque to the proximal end of the torque member;
    an inflation conduit formed over the flexible tube and disposed helically about at least a distal portion of the exterior of the flexible tube; and
    an inflatable balloon located at the distal end of the flexible tube and connected to receive inflation medium from the inflation tube, whereby the helical disposition of the inflation conduit lessens resistance when the catheter is being rotated in a vascular lumen.

11. A vascular catheter as in claim 10, wherein the inflation tube conduit is a separate tube which is secured to the flexible tube by a sheath constricted about the flexible tube and the tube.

12. A vascular catheter as in claim 10, wherein the inflation conduit has a crescent-shaped profile which subtends at least 45° of the periphery of the flexible tube and extends above the surface of the tube by no more than 0.3 of the tube diameter.

13. A vascular catheter as in claim 10, wherein the inflation conduit is wrapped at a helical pitch in the range from about 2 to 20 cm/turn.

14. A vascular catheter as in claim 13, wherein the inflation conduit is arranged helically about only a distal portion of the flexible tube, said distal portion having a length from about 30 to 50 cm.

15. A vascular catheter as in claim 13, wherein the inflation conduit extends over the entire length of the flexible tube.

16. A vascular catheter as in claim 10, further comprising:
    a housing secured to the distal end of the flexible tube, and
    means for severing atheroma disposed on one side of the distal housing,
    wherein the inflatable balloon is disposed on a side of the housing generally opposite to the side on which the severing means is disposed.

17. A vascular catheter as in claim 16, wherein the housing has an elongate aperture on said one side and means for severing includes a cutting blade disposed in the housing and attached to a drive cable disposed in the central lumen of the flexible tube.

18. A vascular catheter as in claim 16, wherein the inflatable balloon is formed as an expanded section of the inflation tube.

19. A vascular catheter comprising:
    a torsionally reinforced flexible tube having at least first and second lumens formed integrally therein and extending from a proximal end to a distal end thereof; and
    an inflatable balloon disposed at the distal end of the flexible tube,
    wherein the first lumen has a substantially circular profile and is disposed axially within the flexible tube and the second lumen is arranged helically about at least a distal portion of the first lumen and is connected at its distal end to the inflatable balloon.

20. A vascular catheter as in claim 19, wherein the second lumen is expanded at its distal end to form the inflatable balloon.

21. A vascular catheter as in claim 19, wherein the first lumen has a diameter in the range from about 0.010 in. to 0.10 in and the second lumen has a diameter in the range from about 0.015 in. to 0.040 in.

22. A vascular catheter as in claim 19, wherein the second lumen has a crescent-shaped profile which subtends at least 45° of the periphery of the first lumen and extends above the surface of the first lumen by no more than 0.3 of the lumen diameter.

23. A vascular catheter as in claim 19, wherein the second lumen has a helical pitch in the range from about 2 to 20 cm/turn.

24. A vascular catheter as in claim 23, wherein the inflation conduit is arranged helically about only a distal portion of the flexible tube, said distal portion having a length from about 30 to 50 cm.

25. A vascular catheter as in claim 23, wherein the inflation conduit extends over the entire length of the flexible tube.

26. A vascular catheter as in claim 19, further comprising:
   a housing secured to the distal end of the flexible tube, and
   means for severing atheroma disposed on one side of the distal housing;
   wherein the inflatable balloon is disposed on a side of the housing generally opposite to the side on which the severing means is disposed.

27. A vascular catheter as in claim 25, wherein the housing has an elongate aperture on said one side and means for severing includes a cutting blade disposed in the housing and attached to a drive cable disposed in the first lumen of the flexible tube.

* * * * *